United States Patent [19]

Uang et al.

[11] Patent Number: 6,054,065
[45] Date of Patent: Apr. 25, 2000

[54] CHIRAL LIGAND AND METHOD FOR PREPARING CYANOHYDRINS FROM ALDEHYDES

[76] Inventors: Biing-Jiun Uang, 4F., No. 2 Alley 120, Qian-Gang St., Baili, Shihlin, Taipei; Chyuan-Der Hwang, No. 65, ShengLi, Miaoli, both of Taiwan

[21] Appl. No.: 09/356,357

[22] Filed: Jul. 19, 1999

[30] Foreign Application Priority Data

Jul. 24, 1998 [TW] Taiwan .................................. 87112176

[51] Int. Cl.$^7$ ........................... C09K 3/00; C07C 253/00; C07C 211/00
[52] U.S. Cl. ....................... 252/183.13; 558/351; 564/461
[58] Field of Search ....................... 252/183.13; 558/351; 564/461

[56] References Cited

U.S. PATENT DOCUMENTS 5,187,296  2/1993  Becker et al. ........................... 558/351

OTHER PUBLICATIONS

Hayashi et al, Asymetric Carbon—Carbon Bond Forming Reactions Catalyzed by Chiral Schiff Base—Titanium Alkoxide Complexes, Tetrahedron, 4385–4398, 1994.

*Primary Examiner*—Johann Richter
*Assistant Examiner*—Joseph Murray
*Attorney, Agent, or Firm*—Bacon & Thomas, PLLC

[57] ABSTRACT

A chiral ligand of the formula (I) or formula (I'),

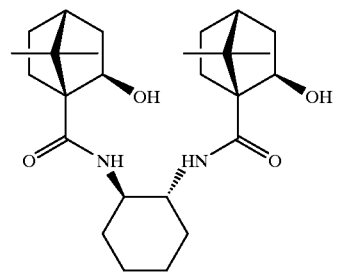

(I)

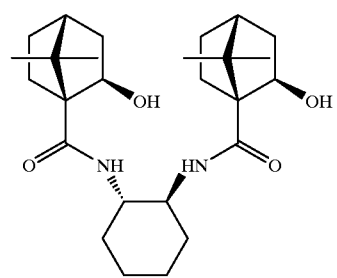

(I')

was synthesized. The chiral ligand (I) or formula (I') can chelate to metals to form a catalytic complex to catalyze the addition of trimethylsilyl cyanide to aldehydes to give optically active cyanohydrin, each individually.

6 Claims, No Drawings

CHIRAL LIGAND AND METHOD FOR PREPARING CYANOHYDRINS FROM ALDEHYDES

FIELD OF THE INVENTION

The present invention relates to chiral ligands, especially relates to novel chiral ligands complex with Ti(OPr)$_4$ to catalyze the asymmetric addition of trimethylsilyl cyanide to aldehydes to give optically active α-cyanohydrins.

BACKGROUND OF THE INVENTION

Optically pure α-cyanohydrins are versatile synthetic intermediates, the two functional groups being easily manipulated into a wide range of other chiral products such as α-hydroxy acids, α-hydroxy aldehydes, α-hydroxy ketones, β-hydroxy amines and α-amino acid derivatives etc.

The usual synthetic route to cyanohydrins was invented more than one hundred years ago. However, the cyanohydrin produced by this well known way is a racemic product. If optically active cyanohydrin is needed for further mulipuulations, additional resolution step(s) for the racemic cyanohydrin would be required. To overcome this problem, several asymmetrical syntheses of cyanohydrin have been developed. Most of these asymmetrical syntheses use a chiral catalyst to induce the formation of just one enantiomer of the cyanohydrin. So far, a number of different catalysts have been investigated, including enzymes, polymeric reagents, peptides and organometallic species. Among them, organometallic species are the catalysts developed recently.

Organometallic species, which were used as the catalysts to catalyze the asymmetrical addition of trimethylsilyl cyanide to aldehydes, were disclosed in several technical literatures. However, drawbacks could also be found among these organometallic species. For example, the organometallic complexes of binaphthaol and titanium tetraisopropoxide, which are reported by Nakai et al., have good enantioselectivity but only for aromatic aldehydes. The organometallic complexes reported by Jiang et al. have enatioselectivity but are easily deteriorated by acids. Bolm et al. also reported organometallic complexes with good enantioselectivity, but stoichiometric amounts of the organometallic complexes catalyst were required.

SUMMARY OF THE INVENTION

The present invention relates to a novel chiral ligand of the formula (I)

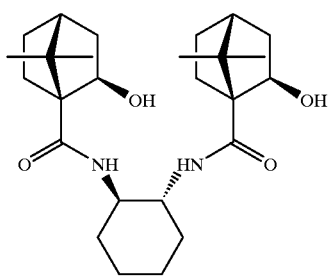

(I)

The organometallic complex catalyst formed from chiral ligand (I) and titanium tetraisopropoxide could catalyze the addition of trimethylsilyl cyanide to give optically active cyanohydrin in the presence of molecular sieves 4 Å at −78° C. In addition, the used chiral ligands could be retrieved from the reaction mixture for recycling.

For catalyzing the synthesis of the asymmetric addition of trimethylsilyl cyanide to aldehydes and give optically active cyanohydrins, only catalytic amounts of the chiral ligand (I) of the present invention are required. The organometallic complexes catalyst containing the chiral ligand (I) of the present invention has acceptable enantioselectivities for all kinds of aldehydes. High enantioselectivities could be observed for aliphatic aldehydes and aromatic aldehydes. In addition, the chiral ligand (I) of the present invention is not deteriorated by acids.

The present invention also relates to a novel diastereomer of the formula (I') of the chiral ligands of the formula (I):

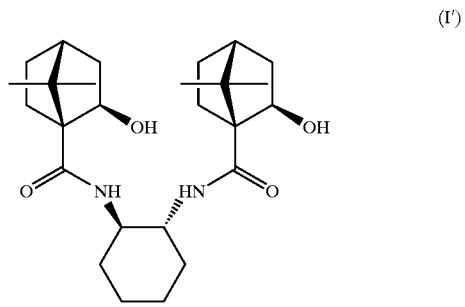

(I')

The acting point of ligand (I') is around 225° C., which is different from that of ligand (I). The synthesis and the application of the novel ligand (I') is very similar to those of the ligand (I). Anyone who is familiar with these arts could understand and derive the application and the synthesis of ligand (I') according to the application and the synthesis of ligand (I) disclosed in the description of the present invention.

DESCRIPTION OF THE PREFERRED EMBODIMENTS

The chiral ligand (I) of the present invention was synthesized by the following procedures. First, ketopinic acid chloride was used to react with trans-(1R,2R)-diaminocyclohexane. After the product of the above reaction was purified, the keto group of the purified product was further reduced to give the chiral ligand (I).

The ligand (I) of the present invention can be used for the synthesis of cyanohydrin by the following procedures: The chiral ligand (I) of the present invention was mixed with molecular 4 Å powders and titanium tetraisopropoxide (Ti(OPr)$_4$). After fully stirring, trimethylsilyl cyanide was added to the reaction mixture. After the temperature of the reaction mixture was cooled to −78° C., aldehyde was added into the reaction mixture. Then optically active cyanohydrin can be obtained after purification.

More detailed examples are used to illustrate the present invention, and these examples are used to explain the present invention. The examples below, which are given simply by way of illustration, must not be taken to limit the scope of the invention.

Preparation 1

The Preparation of Compound (2a)

(1R,2R)-N,N'-di[(1S,4R)-7,7-dimethyl-2-ketonyldicyclo[2.2.1]heptylformyl]-1,2-cyclohexyldiamine (2a)

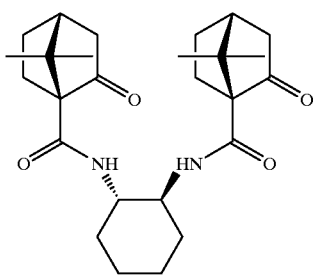

(2a)

Ketopinic acid chloride (10.0 mmol) in $CH_2Cl_2$ was added to a stirred solution of trimethylamine (20.0 mmol), optically active trans-(1R,2R)-1,2-diamino-cyclohexane and $CH_2Cl_2$(100 ml) at 0° C. over 1 hour period. After stirring for another 1 hour, deionized water was added to the mixture. The mixture was then neutralized and extracted with $CH_2Cl_2$. The $CH_2Cl_2$ layer was then washed with brine (2×100 ml), dried, filtered, concentrated and purified by column chromatography to furnish compound (2a), as a white solid, mp 153° C.

$^1$H NMR (400 MHz, $CDCl_3$): δ 7.43(d, J=8Hz, 2H), 3.76–3.81(m, 2H), 2.40–2.49(m, 4H), 2.01–2.1(m, 6H), 1.90 (d, J=20 Hz, 2H), 1.65–1.70(br s, 4H), 1.47–1.54(m, 2H), 1.2–1.39(m, 4H), 1.18(s, 6H), 0.96(s, 6H)

$^{13}$C NMR(100 MHz, $CDCl_3$): δ 215.76, 168.97, 64.17, 52.25, 49.70, 43.55, 43.18, 32.55, 27.89, 27.41, 24.50, 20.67, 20.35.

IR (KBr) $v_{max}$($cm^{-1}$):3323, 2936, 1732, 1659, 1543.

LRMS(EL, 70eV)m/z(%): 442(M+,0.68%), 261(100%), 165(27%), 96(65%) HRMS: $C_{26}H_{38}O_4N_2$

Calcd for $C_{26}H_{38}O_4N_2$: 442.2832. Found: 442.2846.

Elementary Analysis: Calcd for $C_{26}H_{38}O_4N_2$: C, 70.56; H, 8.65; N, 6.33. Found: C, 70.46; H, 8.58; N, 6.24

Preparation 2

The Preparation of Compound (I)

(1R, 2R)-N,N'-di[(1S,2R,4R)-7,7-dimethyl-2-hydroxy-dicyclo[2.2.1]heptyl formyl]-1,2-cyclohexyldiamine (I)

To a solution of (2a) (4 mmol) in THF(5 ml) at −78° C. was dropwise added 1 N L-selectride® in THF(18.0 ml). The reaction mixture was stirred at −78° C. for 2 h followed by 1 h at room temperature. Then, the reaction mixture was cooled to 0° C. and quenched by the successive addition of EtOH (12 ml), 3 N aq. NaOH (16 ml), followed by the dropwise addition of 30% $H_2O_2$ (12 ml) over a 30 min. period. The aqueous phase was saturated with $K_2CO_3$ and extracted with $CH_2Cl_2$. The organic phase was dried with $Na_2SO_4$, filtered and concentrated to furnish compound (I), as a white solid, mp 208° C.

$^1$H NMR (400 MHz, $CDCl_3$): δ 6.89(d, J=9Hz, 2H), 5.207.43(d, J=6Hz, 2H), 3.70–3.76(m, 2H), 2.30–2.38(m, 2H), 1.67–1.95(m, 2H), 1.16–1.40(m, 4H), 1.14(s, 6H), 0.90–1.02(m, 4H), 0.85(s, 6H)

$^{13}$C NMR (100 MHz, $CDCl_3$): δ173.79, 77.39, 58.44, 53.42, 49.52, 45.45, 40.97, 32.35, 28.96, 26.33, 24.86, 20.98, 20.85.

IR (KBr) $v_{max}$($cm^{-1}$):3535, 3328, 1629, 1564, 1065, 1029.

LRMS(EL, 70eV)m/z(%): 446($M^+$, 1.93%), 263(34%), 149(25%), 97(100%) HRMS: $C_{26}H_{38}O_4N_2$

Calcd for $C_{26}H_{42}O_4N_2$: 442.3145. Found: 442.3136.

Elementary Analysis: Calcd for $C_{26}H_{38}O_4N_2$: C, 69.92; H, 9.48; N, 6.27. Found: C, 69.67; H, 9.55; N, 6.28.

The following examples (1–9) are the applications of the chiral ligands of the present invention.

EXAMPLE 1

To a stirred solution of compound (I) (0.147 g, 0.33 mmol) and molecular sieve 4 Å (powder, 130 mg) in dichloromethane (5 ml) was added titanium tetraisopropoxide (0.09 ml, 0.3 mmol) under argon at room temperature, and stir for 1 hour. Trimethylsilyl cyanide (0.45 ml, 3.5 mmol) was added to the reaction mixture and stirred for an additional 0.5 hour. Then, the reaction mixture was cooled to −78° C. and benzaldehyde (0.2 ml, 2 mmol) was added to the reaction mixture. The disappearance of the aldehyde was monitored by thin layer chromatography (ethyl acetate/hexane=1/5). The reaction mixture was quenched with 1 N HCl (20 ml) and stirred vigorously at room temperature for 6 h. After filtering, the mixture was extracted with dichloromethane (5×5 ml). The combined organic extracts were washed with brine and dried over anhydrous $Na_2SO_4$, then concentrated. The residue was distilled under reduced pressure (100° C./0.3 mmHg) to give (S)-cyanohydrin (79%, 94% e.e. (enantiomeric excess)). Compound (I) was recovered in 92% yield through column purification of the remaining residue.

EXAMPLE 2 TO 9

The procedures and reagents used for preparing cyanohydrin in example 2 to 9 are as same as those in example 1 except the aldehydes in example 1 were replaced by the aldehydes listed in table 1. The result are also shown in table 1.

TABLE 1

| Example | aldehyde | Cyanohydrin | Yield (%)[a] | e.e. (%) | configuration |
| --- | --- | --- | --- | --- | --- |
| 1 | Benzaldehyde | 2-hydroxy-2-phenylacetonitrile | 79 | 94 | S |
| 2 | 2-methyl benzaldehyde | 2-hydroxy-2-(2-methylphenyl) acetonitrile | 68 (85) | 97.3 | S |
| 3 | 3-phenoxy benzaldehyde | 2-hydroxy-2-(3-phenyoxyphenyl) acetonitrile | 57 (76) | 97.2 | S |

TABLE 1-continued

| Example | aldehyde | Cyanohydrin | Yield (%)[a] | e.e. (%) | configuration |
|---|---|---|---|---|---|
| 4 | 4-methoxy benzaldehye | 2-hydroxy-2-(4-methoxyphenyl) acetonitrile | 53 (75) | 96.6 | S |
| 5 | 2-naphthaldehyde | 2-hydroxy-2-naphthyl, acetonitrile | 76 (85) | 96.2 | S |
| 6 | (E)-cinnamaldehyde | (E)-2-hydroxy-4-phenyl-3-butenylnitrile | 51 (80) | 95.9 | S |
| 7 | 3-phenylpropion-aldehyde | 2-hydroxy-4-phenyo butylnitrile | 62 (78) | 97.5 | S |
| 8 | cyclo-hexane-carboxaldehyde | 2-cyclohexyl-2-hydroxy-2-acetonitrile | 94 | 87.2 | S |
| 9 | valeraldehyde | 2-hydroxy-hexyinitrile | 96 | 88.5 | S |

[a]Numbers in parentheses are percent conversions

The comparison of the yields and the enantioselectivities of the ligand of the present invention and some other ligands disclosed before were shown in table 2. As shown in table 2, the addition of trimethylsilyl cyanide to benzaldehyde by using the complex formed from titanium tetraisopropoxide [Ti(OPr)$_4$] and the ligand of the present invention as the catalyst is highly enantioselective. Only a small amount of catalyst is needed for the addition of trimethylsilyl cyanide to benzaldehyde. Furthermore, the recovery of the ligand of the present invention is also high (92%).

TABLE 2

| Comparative example | ligand (mol %) | Organometal (mol %) | Yield (%) | e.e. (%) | config-uration |
|---|---|---|---|---|---|
| 1 | (I) (16.5) | Ti(O$^i$Pr)$_4$(15) | 79 | 94 | S |
| 2 | A (20) | Ti(O$^i$Pr)$_4$(20) | >90 | <10 | S |
| 3 | B (40) | Ti(O$^i$Pr)$_4$(20) | 72 | 92 | S |
| 4 | C (10) | Ti(O$^i$Pr)$_4$(100) | 72 (96) | 91 | S |

The structures of compounds (A), (B), (C) and (I) are shown below:

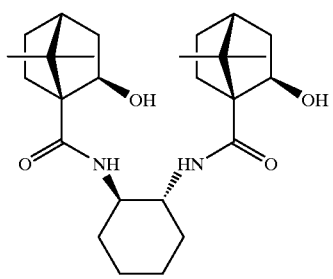
(I)

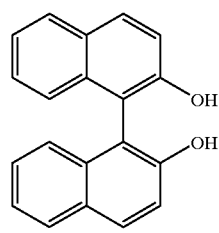
(A)

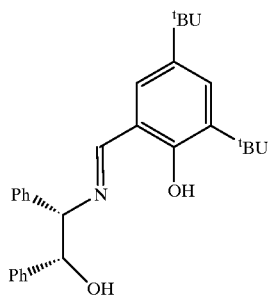
(B)

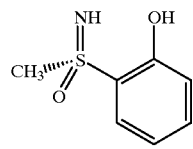
(C)

From the foregoing description, one skilled in the art can easily ascertain the essential characteristics of this invention, and, without departing from the scope thereof, can make various changes and modifications of the invention to adapt it to various usages and conditions. Thus, other embodiments are also within the claims.

What is claimed is:

1. A chiral compound of the formula (I) or formula (I'),

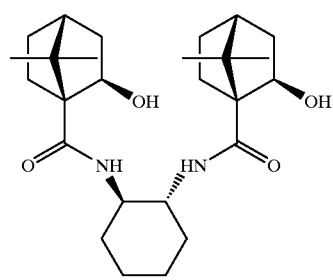
(I)

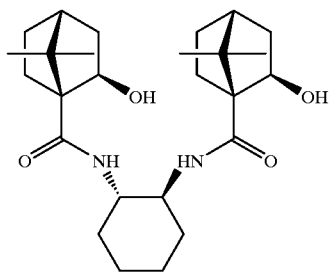 (I')

2. An organometallic catalyst complex comprising [Ti(OPr)$_4$] and the chiral compound of claim 1.

3. A process for preparing cyanohydrins from aldehydes, which is characterized by applying the organometallic catalyst complex of claim 2 as the catalyst to catalyze the addition of trimethylsilyl cyanide to aldehydes to give optically active hydroxylcyanides.

4. The process of claim 3, wherein the addition proceeds in the presence of a 4 Å molecular sieve.

5. The process of claim 3, wherein the aldehydes are aliphatic aldehydes.

6. The process of claim 3, wherein the aldehydes are aromatic aldehydes.

* * * * *

UNITED STATES PATENT AND TRADEMARK OFFICE
CERTIFICATE OF CORRECTION

PATENT NO. : 6,054,065
DATED : April 25, 2000
INVENTOR(S) : Biing-Jiun Uang; Chyuan-Der Hwang It is certified that error appears in the above-identified patent and that said Letters Patent is hereby corrected as shown below:

Add the Assignee item [73] as noted below:

Everlight USA, Inc.
Pineville, North Carolina 26134 USA

Signed and Sealed this

Twelfth Day of June, 2001

*Attest:*

*Attesting Officer*

NICHOLAS P. GODICI
*Acting Director of the United States Patent and Trademark Office*